United States Patent [19]
Schwan et al.

[11] 3,966,758
[45] June 29, 1976

[54] ANTI-INFLAMMATORY 1-(SUBSTITUTED BENZYL)-2-IMIDAZOLIDINONES

[75] Inventors: Thomas J. Schwan; Nelson J. Miles, both of Norwich, N.Y.

[73] Assignee: Morton-Norwich Products, Inc., Norwich, N.Y.

[22] Filed: June 16, 1975

[21] Appl. No.: 586,921

[52] U.S. Cl............... 260/309.7; 260/618 D; 260/651 HA; 424/273
[51] Int. Cl.² ........................................ C07D 49/34
[58] Field of Search ................................ 260/309.7

[56] References Cited
UNITED STATES PATENTS

| | | |
|---|---|---|
| 2,514,380 | 7/1950 | Duschinsky................ 260/309.7 |
| 3,196,152 | 7/1965 | Wright, Jr. et al............ 260/309.7 X |
| 3,459,757 | 8/1969 | Wright, Jr. et al............ 260/309.7 X |
| 3,636,039 | 1/1972 | Gruenman et al.............. 260/309.7 |
| 3,876,657 | 4/1975 | Aelony et al. .................. 260/309.7 |

*Primary Examiner*—Ethel G. Love
*Attorney, Agent, or Firm*—Anthony J. Franze

[57] ABSTRACT

Certain 1-(substituted benzyl)-2-imidazolidinones of the formula:

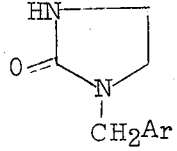

wherein Ar is 4-chlorophenyl, 3-fluorophenyl, 2,3-dichlorophenyl, and 1-naphthyl possess pharmacological activity as anti-inflammatory agents.

5 Claims, No Drawings

3,966,758

ANTI-INFLAMMATORY 1-(SUBSTITUTED BENZYL)-2-IMIDAZOLIDINONES

This invention relates to chemical compounds. In particular it is concerned with compounds of the formula:

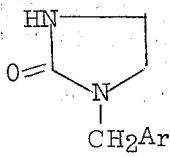

wherein Ar is 4-chlorophenyl, 3-fluorophenyl, 2,3-dichlorophenyl, and 1-naphthyl. These compounds possess pharmacological activity. They are particularly useful as anti-inflammatory agents as evidenced by their ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited [Winter et al., P.S.E.B.M. 14:544 (1964)].

The preparation of the compounds of this invention can be accomplished according to the following scheme:

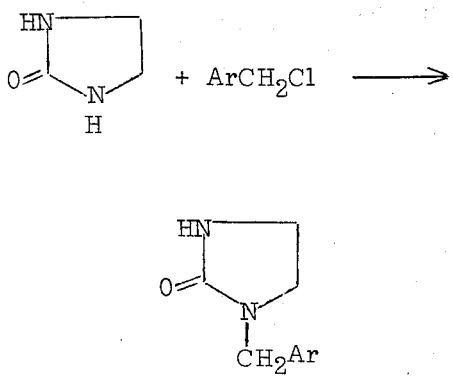

In this scheme Ar has the significance previously ascribed. The reaction is conducted in the presence of a base such as potassium carbonate and a catalyst such as potassium iodide. A solvent inert under the conditions of the reaction such as dimethylformamide or dimethylsulfoxide is employed.

In order that this invention be readily available to and understood by those skilled in the art the following examples are included:

EXAMPLE I

1(4-Chlorobenzyl)-2-imidazolidinone

A 21.5 g (0.25 mole) portion of 2-imidazolidinone in 300 ml of dimethylsulfoxide was treated with 34.5 g (0.25 mole) of potassium carbonate, 10 g (0.06 mole) of potassium iodide and 40.5 g (0.25 mole) of 4-chlorobenzyl chloride. The reaction mixture was heated to 100° over 0.3 hours, held at 100° with rapid stirring for 1.3 hours and poured into 1.3 l of water. The aqueous mixture was extracted with 1.3 l of chloroform. The chloroform extract was washed with 150 ml of water, dried over magnesium sulfate for 3 hours and filtered. The filtrate was concentrated to dryness to give 49 g (92%) a light yellow oil which crystallized.

The crude product was recrystallized from 60 ml of acetonitrile, washed with ether, and air dried, m.p. 164°–166°. Yield: 10.6 g (19%).

Anal. Calcd. for $C_{10}H_{11}ClN_2O$: C, 57.01; H, 5.26; N, 13.30. Found: C, 56.73; H, 5.25; N, 13.22.

EXAMPLE II

1-(3-Fluorobenzyl)-2-imidazolidinone

A 21.5 g (0.25 mole) portion of 2-imidazolidinone in 150 ml of dimethylsulfoxide was treated with 34.5 g (0.25 mole) of potassium carbonate, 20 g (0.12 mole) of potassium iodide and 36.3 g (0.25 mole) of 3-fluorobenzyl chloride. The reaction mixture was heated with rapid stirring to 100° over 0.3 hours, held at 100° for 1.8 hours and poured with rapid stirring into 1.5 l of cold water. The aqueous mixture was extracted with 1.3 l of chloroform. The chloroform extract was washed with 500 ml of water, dried over magnesium sulfate overnight and filtered. The filtrate was concentrated to dryness to give 46 g (94%) of a light green semi-solid. The crude product was washed with 125 ml of ether, filtered and air dried to give 13.5 g (28%) of a white solid, m.p. 103°–105°.

Anal. Calcd. for $C_{10}H_{11}FN_2O$: C, 61.84; H, 5.71; N, 14.43. Found: C, 61.98; H, 5.72; N, 14.62.

EXAMPLE III

1-(1-Naphthylmethyl)-2-imidazolidinone

A 21.5 g (0.25 mole) portion of 2-imidazolidinone in 250 ml of dimethylsulfoxide was treated with 34.5 g (0.25 mole) of potassium carbonate, 20.0 g (0.12 mole) of potassium iodide and 44.3 g (0.25 mole) of 1-(chloromethyl)-naphthalene. The reaction mixture was heated at 105° over 0.3 hours, held at 105° for 1.7 hours, poured with rapid stirring into 1.5 l of cold water, stirred for 1 hour and filtered. The off-white solid was washed with ether, air dried, and dried to a constant weight at 90°, m.p. 147°–151°. Yield: 40 g.

The crude product was recrystallized from 650 ml of methanol to give 12 g of 1,3 bis (1-naphthylmethyl)-2-imidazolidinone.

Concentration of the methanolic filtrate to one-fifth volume and subsequent cooling and filtration gave 24 g (43%) of 1-(1-naphthylmethyl)-2-imidazolidinone, m.p. 121°–125°.

The crude product was recrystallized from 80 ml of methanol, washed with 50 ml of ether and air dried to give 13 g (23%) of a white solid, m.p. 153°–155°.

Anal. Calcd. for $C_{14}H_{14}N_2O$: C, 74.31; H, 6.24; N, 12.38. Found: C, 74.32; H, 6.25; N, 12.15.

EXAMPLE IV

A. 2,3-Dichlorobenzyl alcohol

A 20.0 (0.105 mole) portion of 2,3-dichlorobenzoic acid in 100 ml of toluene was treated with 254 ml (0.315 mole) of diisobutylaluminum hydride (25% in hexane), under a stream of dry nitrogen, at 15°–20° over 0.5 hours using rapid stirring. The reaction mixture was allowed to warm to room temperature over 0.5 hours, heated to reflux over 0.5 hours, refluxed for 1.5 hours, allowed to cool slowly to room temperature, and stored overnight at room temperature. The reaction mixture was then treated with a solution of 100 ml of methanol in 100 ml of water at 10°–15°, followed by 100 ml of concentrated hydrochloric acid at 20°–25°, and 165 ml of water. The organic layer was separated, washed with 50 ml of 5% sodium bicarbonate, 50 ml of water, dried over magnesium sulfate overnight and filtered. The filtrate was concentrated to dryness to given 17.0 g (91%) of a light tan solid, m.p. 81°–84°.

B. 2,3-Dichlorobenzyl chloride

A 17.0 g (0.096 g) portion of IV-A in 150 ml of chloroform was treated at minus 10–0° with 35 ml (57.5 g, 0.48 mole) of thionyl chloride, allowed to warm to 20° over 0.5 hours, heated to reflux over 0.5 hours, and refluxed for 1.5 hours. The reaction mixture was filtered and concentrated under reduced pressure to give 18.7 g (99%) of a light yellow viscous oil.

C. 1-(2,3-Dichlorobenzyl)-2-imidazolidinone

A 8.3 g (0.097 mole) portion of 2-imidazolidinone in 80 ml of dimethylsulfoxide was treated with 13.4 g (0.097 mole) of potassium carbonate, 7.6 g (0.055 mole) of potassium iodide and 18.7 g (0.096 mole) of IV-B. The reaction mixture was heated to 105° over 0.5 hours, held at 105° for 1.7 hours, poured into 750 ml of water and extracted with 700 ml of chloroform. The chloroform extract was washed with 250 ml of water, dried over magnesium sulfate overnight and filtered. The filtrate was concentrated under reduced pressure to give 13.5 g (57%) of a light yellow oil.

The crude product was washed with 150 ml of heptane followed by two 50 ml portions of ether to give 4.0 g (17%) of a white solid, m.p. 106°–110°.

The white solid was recrystallized from 20 ml of benzene, washed with 10 ml of ether, air dried and dried to a constant weight at 100°, m.p. 110°–113°. Yield: 1.0 g (4%).

The filtrate was concentrated to one-fifth volume to give an additional 2.0 g (8%) of a white solid, m.p. 110°–113°.

Anal. Calcd. for $C_{10}H_{10}Cl_2N_2O$: C, 49.00; H, 4.11; N, 11.43. Found: C, 49.08; H, 4.24; N, 11.54.

What is claimed is:

1. A compound of the formula:

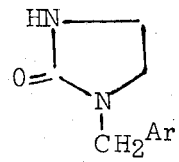

wherein Ar is 4-chlorophenyl, 3-fluorophenyl, 2,3-dichlorophenyl, and 1-naphthyl.

2. The compound 1-(4-chlorobenzyl)-2-imidazolidinone.

3. The compound 1-(3-fluorobenzyl)-2-imidazolidinone.

4. The compound 1-(1-naphthylmethyl)-2-imidazolidinone.

5. The compound 1-(2,3-dichlorobenzyl)-2-imidazolidinone.

* * * * *